(12) United States Patent
Lee et al.

(10) Patent No.: US 9,234,171 B2
(45) Date of Patent: Jan. 12, 2016

(54) STEM CELL DIFFERENTIATION USING NOVEL LIGHT-RESPONSIVE HYDROGELS

(75) Inventors: Ki-Bum Lee, Monmouth Junction, NJ (US); Shreyas Shah, Dayton, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 140 days.

(21) Appl. No.: 13/314,891

(22) Filed: Dec. 8, 2011

(65) Prior Publication Data
US 2012/0149781 A1 Jun. 14, 2012

Related U.S. Application Data

(60) Provisional application No. 61/420,793, filed on Dec. 8, 2010.

(51) Int. Cl.
| | |
|---|---|
| *C12N 5/071* | (2010.01) |
| *C12N 5/00* | (2006.01) |
| *A61K 47/30* | (2006.01) |
| *C12N 5/079* | (2010.01) |

(52) U.S. Cl.
CPC .......... *C12N 5/0618* (2013.01); *C12N 2506/45* (2013.01); *C12N 2529/10* (2013.01); *C12N 2533/30* (2013.01); *C12N 2533/50* (2013.01); *C12N 2535/10* (2013.01); *C12N 2537/10* (2013.01)

(58) Field of Classification Search
None
See application file for complete search history.

(56) References Cited

U.S. PATENT DOCUMENTS

| | | | |
|---|---|---|---|
| 5,482,719 A * | 1/1996 | Guillet et al. ................. | 424/486 |
| 2003/0013192 A1* | 1/2003 | Laeng et al. ................... | 435/368 |
| 2006/0121535 A1* | 6/2006 | Brueggemeier et al. ....... | 435/7.1 |
| 2006/0210527 A1* | 9/2006 | Davis ......................... | 424/78.27 |

OTHER PUBLICATIONS

Lin et al. PEG Hydrogels for the Controlled Release of Biomolecules in Regenerative Medicine. Pharmaceutical Research, 2009. 26(3): 631-643.*
Suter et al. Neural Commitment of Embryonic Stem Cells: Molecules, Pathways and Potential for Cell Therapy. Journal of Pathology, 2008. 215:355-368.*
Hersel et al. RGD Modified Polymers: Biomaterials for Stimulated Cell Adhesion and Beyond. Biomaterials. 2003. 24:4385-4415.*
Amabile et al., "Induced pluripotent stem cells: current progress and potential for regenerative medicine," Trends in Molecular Medicine, (2009) vol. 15(2): pp. 59-68 (Abstract only).
Aujard et al., "o-Nitrobenzyl Photolabile Protecting Groups with Red-Shifted Absorption: Syntheses and Uncaging Cross-Sections for One- and Two-Photon Excitation," Chemistry—A European J., (2006) vol. 12(26) pp. 6865-6879 (Abstract only).
Axell et al., "A method for rapid derivation and propagation of neural progenitors from human embryonic stem cells," J. Neurosci. Meth., (2009) vol. 184(2), pp. 275•-284 (Abstract only).
Borghese et al., "Inhibition of Notch Signaling in Human Embryonic Stem Cell-Derived Neural Stem Cells Delays G1/S Phase Transition and Accelerates Neuronal Differentiation in Vitro and in Vivo," Stem Cells, (2010) vol. 28, pp. 955-964.
Domke et al., "Measuring the Elastic Properties of Thin Polymer Films with the Atomic Force Microscope," Langmuir, (1998) vol. 14, pp. 3320-3325 (Abstract only).
Fedorovich et al., "The effect of photopolymerization on stem cells embedded in hydrogels," Biomat., (2009) vol. 30, pp. 344-353 (Abstract only).
Fomina et al., "UV and Near-IR Triggered Release from Polymeric Nanoparticles," J. Am. Chem. Soc., (2010), vol. 132, pp. 9540-9542 (Abstract only).
Furuta et al., "Brominated 7-hydroxycoumarin-4-ylmethyls: Photolabile protecting groups with biologically useful cross-sections for two photon photolysis," Proc. Natl. Acad. Sci. USA., (1999) vol. 96, pp. 1193-1200 (Abstract only).
Gopin et al., "A chemical adaptor system designed to link a tumor-targeting device with a prodrug and an enzymatic trigger," Angew. Chem. Int. Ed., (2003) vol. 42, pp. 327-332 (Abstract only).
Gupta et al., "A versatile approach to high-throughput microarrays using thiol-ene chemistry," Nat. Chem., (2010) vol. 2, pp. 138-145 (Abstract only).
Hall, P.E., et al., "Laminin enhances the growth of human neural stem cells in defined culture media," BMC Neurosci., (2008) vol. 9, p. 71.
Kloxin et al., "In situ elasticity modulation with dynamic substrates to direct cell phenotype," Biomaterials, (2010) vol. 31, pp. 1-8.
Liu, S.Q., et al., "Synthetic hydrogels for controlled stem cell differentiation," Soft Matter, (2010) vol. 6, pp. 67-81 (Abstract only).
Polizzotti et al., "Three-Dimensional Biochemical Patterning of Click-Based Composite Hydrogels via Thiolene Photopolymeriz," Biomacromol., (2008) vol. 9, Iss.4, pp. 1084-1087 (Abstract only).
Ramasamy et al., "Notch Exhibits Ligand Bias and Maneuvers Stage-Specific Steering of Neural Differentiation in Embryonic Stem Cells," Mol. Cell. Biol., (2010) vol. 30, pp. 1946•-1957.
Saha et al., "Substrate Modulus Directs Neural Stem Cell Behavior," Biophys. J., (2008) vol. 95, pp. 4426-4438.
Tan, H., et al., "Novel Multi-arm PEG-based Hydrogels for Tissue Engineering," J. Biomed. Mater. Res. Part A, (2010) vol. 92A, pp. 979-987.
Tibbitt et al., "Hydrogels as Extracellular Matrix Mimics for 3D Cell Culture," Biotech. and Bioeng., (2009) vol. 103, pp. 655-663.
Ulijn et al., "Bioresponsive hydrogels," Materials Today, (2007) vol. 10, pp. 40-48.
Wosnick et al., "Three-dimensional Chemical Patterning of Transparent Hydrogels," Chemistry of Materials, (2007) vol. 20, pp. 55-60.

* cited by examiner

*Primary Examiner* — Maria Leavitt
*Assistant Examiner* — Kimberly A Aron
(74) *Attorney, Agent, or Firm* — Fox Rothschild LLP

(57) ABSTRACT

This application discloses a light-responsive hydrogel-based platform that can modulate multiple microenvironmental signals to direct the differentiation of human induced pluripotent stem cell-derived neural progenitor cells (hiPSC-NPCs) into neuronal cells. The invention provides novel methods for directing differentiation of neural stem cells into neurons useful for treatment of degenerative diseases or disorders, including but not limited to Alzheimer's, Parkinson's, or spinal cord injury (SCI).

15 Claims, 11 Drawing Sheets

STEM CELL DIFFERENTIATION USING NOVEL LIGHT-RESPONSIVE HYDROGELS

CROSS-REFERENCE TO RELATED APPLICATIONS

This application claims priority under 35 U.S.C. §119(e) to U.S. Provisional Patent Application Ser. No. 61/420,793, filed on Dec. 8, 2010, which is hereby incorporated by reference in its entirety.

STATEMENT REGARDING FEDERALLY SPONSORED RESEARCH

The invention described herein was supported in whole or in part by grants from the National Institutes of Health (Grant No. 1DP20D006462-01). The U.S. Government has certain rights in this invention.

FIELD OF THE INVENTION

The present invention relates to novel light-responsive hydrogels and their use for differentiation of stem cells, in particular human induced pluripotent stem cell-derived neural progenitor cells (hiPSC-NPCs) into neurons.

BACKGROUND OF THE INVENTION

Over the last decade, stem cells have gained tremendous attention for applications in regenerative medicine. The inherent ability of stem cells to self-renew and to differentiate into specialized cell types makes them an attractive area of research. Pluripotent stem cells (such as embryonic stem cells and induced pluripotent stem cells) have become especially popular since they can provide cells for essentially every tissue and organ in the body, making them a type of universal cell source. In particular, these cells hold great potential in neuroscience for the treatment of numerous nervous system disorders (e.g. Alzheimer's disease, Parkinson's disease, spinal cord injury) since they provide an unlimited source of engraftable neural cells. While pluripotent stem cells afford great opportunities for exploring the devastating deficiencies in neuro-regenerative medicine, controlling stem cell fate towards specific neuronal cell lineage is one of the most pressing concerns to address before their therapeutic application can be fully realized.

To this end, the cellular microenvironment (composed of soluble signals, insoluble/physical signals and cell-cell interactions) plays a decisive role in regulating stem cell differentiation. However, the function of stem cell microenvironmental factors on differentiation is extremely difficult to investigate since these studies require extensive knowledge of multiple regulatory signals and how they interact to influence cellular function. While generous progress has been made in an attempt to address these concerns, the conventional methods currently available for such an investigation are still limited. At the same time, current therapy has seen the survival of only a small fraction of the stem cells or their differentiated cell types when implanted in vivo, due to inflammation and hypoxia present at the damaged site. In turn, several obstacles such as preparing engraftable homogenous neural cells and improving the ability to precisely control neural cell fate must be surmounted before innovative clinical approaches for neuro-regenerative medicine can be developed.

SUMMARY OF THE INVENTION

The present invention addresses the aforementioned challenges, and involves a bioactive scaffold which can provide considerable control over the microenvironment signals for controlling differentiation into neuronal cells.

This invention provides, in one embodiment, three-dimensional micron-scale patterns of a novel light-responsive hydrogel that is useful for the differentiation of human induced pluripotent stem cell-derived neural progenitor cells (hiPSC-NPCs) into neurons and methods for the neuro-differentiation of hiPSC-derived NPCs in the novel light-responsive hydrogel microenvironment. A three-dimensional culture system has advantages for stem cell differentiation since such a system better mimics the natural cell microenvironment. Hydrogels, in particular, are a preferred biomaterial due to their tissue-like tunable properties.

In one aspect, the present invention provides a light-responsive hydrogel composition for differentiation of stem cells, comprising:
(a) a polyethylene glycol (PEG) hydrogel;
(b) a UV or NIR triggered chemical adaptor system covalently attaching small molecules to the PEG hydrogel; and
(c) small molecules covalently attached to said chemical adaptor system that promote differentiation of neural stem cells into neuronal cells;
wherein said small molecules are cleavable from said chemical adaptor system upon exposure of said system to UV or NIR.

In another aspect, the present invention provides a method for inducing differentiation of pluripotent stem cells into neuronal cells, comprising allowing pluripotent stem cells to infiltrate into a light-responsive hydrogel composition as defined above in a culture medium, and irradiating the hydrogel composition with a UV or NIR light.

In another aspect, the present invention provides a method for treating a neurodegenerative disorder or neurological injury, comprising administering to a subject in need of the treatment a therapeutically effective amount of neuron or neuronal cells encapsulated within a light-responsive hydrogel composition as defined above, wherein the neuronal cells encapsulated are capable of differentiating into desired neurons within the hydrogel composition.

In another aspect, the present invention provides a biocompatible implant comprising neurons or neuronal cells differentiated from pluripotent stem cells in a light-responsive hydrogel composition as defined above that has been exposed to light wavelengths effective to release said small molecules.

In another aspect, the present invention provides a kit for preparation of a light-responsive hydrogel composition, comprising the following pre-polymer components: a) a multi-arm poly(ethylene glycol) (PEG)-thiol macromer; b) a PEG diacrylate monomer; c) an acrylate monomer covalently attached to an adhesion peptide chain; and d) a UV or NIR triggered chemical adaptor covalently attached to small molecules, wherein the pre-polymer components are capable of co-polymerization to form a hydrogel composition under irradiation with a UV light.

Approaches of the invention to neuronal differentiation include: tuning standard culture conditions (e.g. growth media, feeder-layers, etc) (General); altering mechanical properties of the microenvironment (e.g. softer substrates favor neuronal formation) (Mechanical); importance of proper ligand/peptide display (i.e. IKVAV-adhesion peptide promotes neuronal formation) (Biochemical); and use of biomolecules to modulate intrinsic signaling pathways (e.g. inhibit Notch signaling pathway to promote neuronal formation) (Genetic).

Thus, the invention provides synthesis of the ultraviolent (UV)-triggered cross-linking, near infrared (NIR)-degradable, poly (ethylene glycol)-based hydrogel and use of photolithography to generate geometry/dimension-variant 3D micropatterns of the hydrogel.

The present invention provides a new design of hydrogels with multiple tunable properties upon irradiation with ultraviolet light (UV) and near-infrared (NIR) light. The different wavelengths of light are employed in this hydrogel system to generate three-dimensional micron-scale patterns of varying geometries and dimensions, to alter the polymer structure integrity (i.e. cross-linking and degradation), to tune the mechanical properties and to release small molecules that can alter key signaling pathways.

The bioactive scaffold provided by one aspect of the invention offers considerable control over the microenvironment signals for regulating stem cell differentiation into neuronal cells, while enhancing the survival of engrafted cells.

These and other aspects of the present invention will be better appreciated by reference to the following figuress and detailed description.

DETAILED DESCRIPTION OF THE INVENTION

Figure 1:
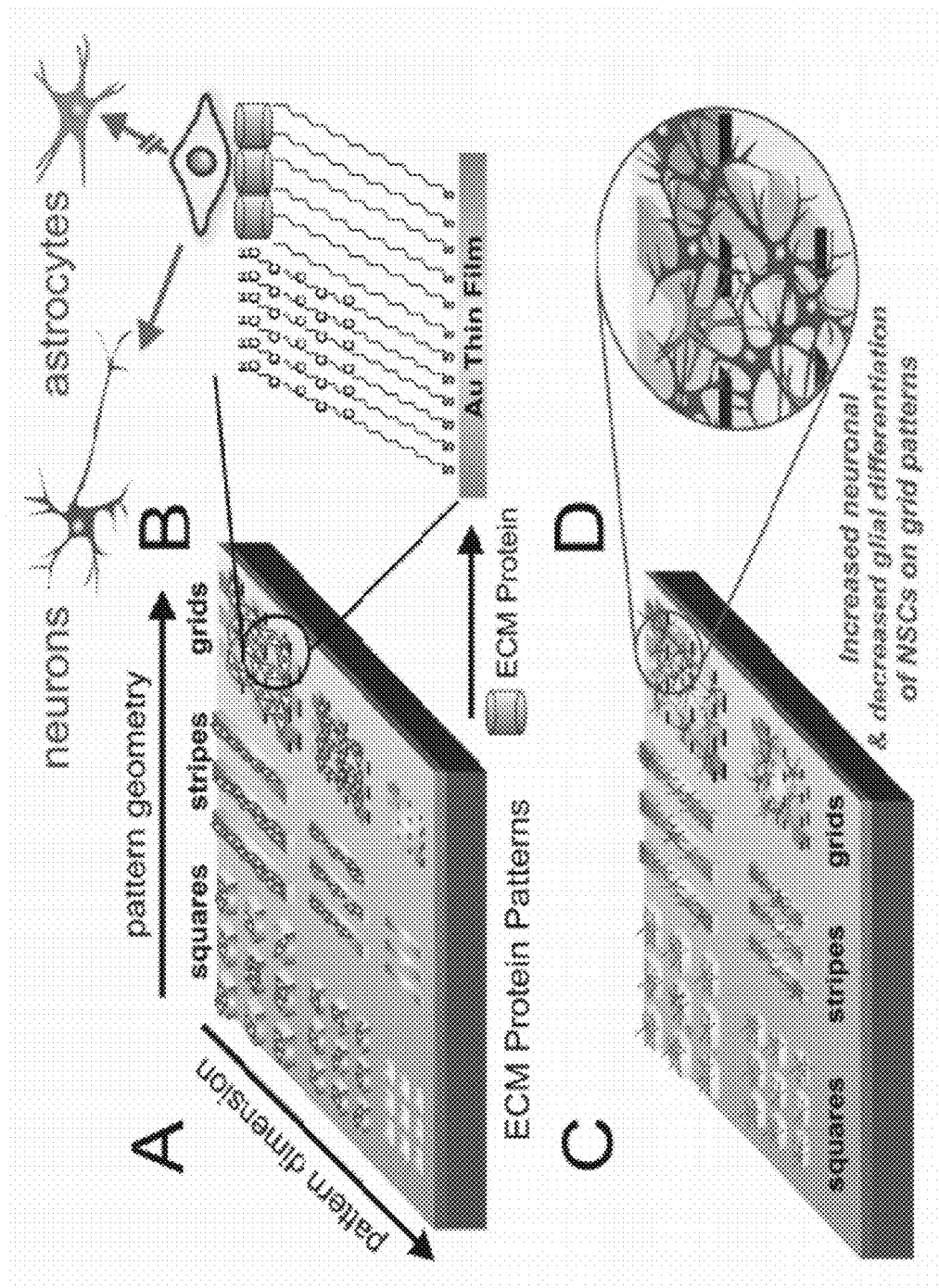
FIG. 1 illustrates a schematic diagram for forming combinatorial ECM arrays. (A) Fabrication and application of ECM protein patterns for NSC differentiation. (B) Selective attachment of NSCs and differentiation into different kinds of neural cells. (C) Differentiation of NSCs into neurons (red) or astrocytes (green). (D) Increased neuro-differentiation on grid patterns as compared to squares and stripes.
Figure 2A:
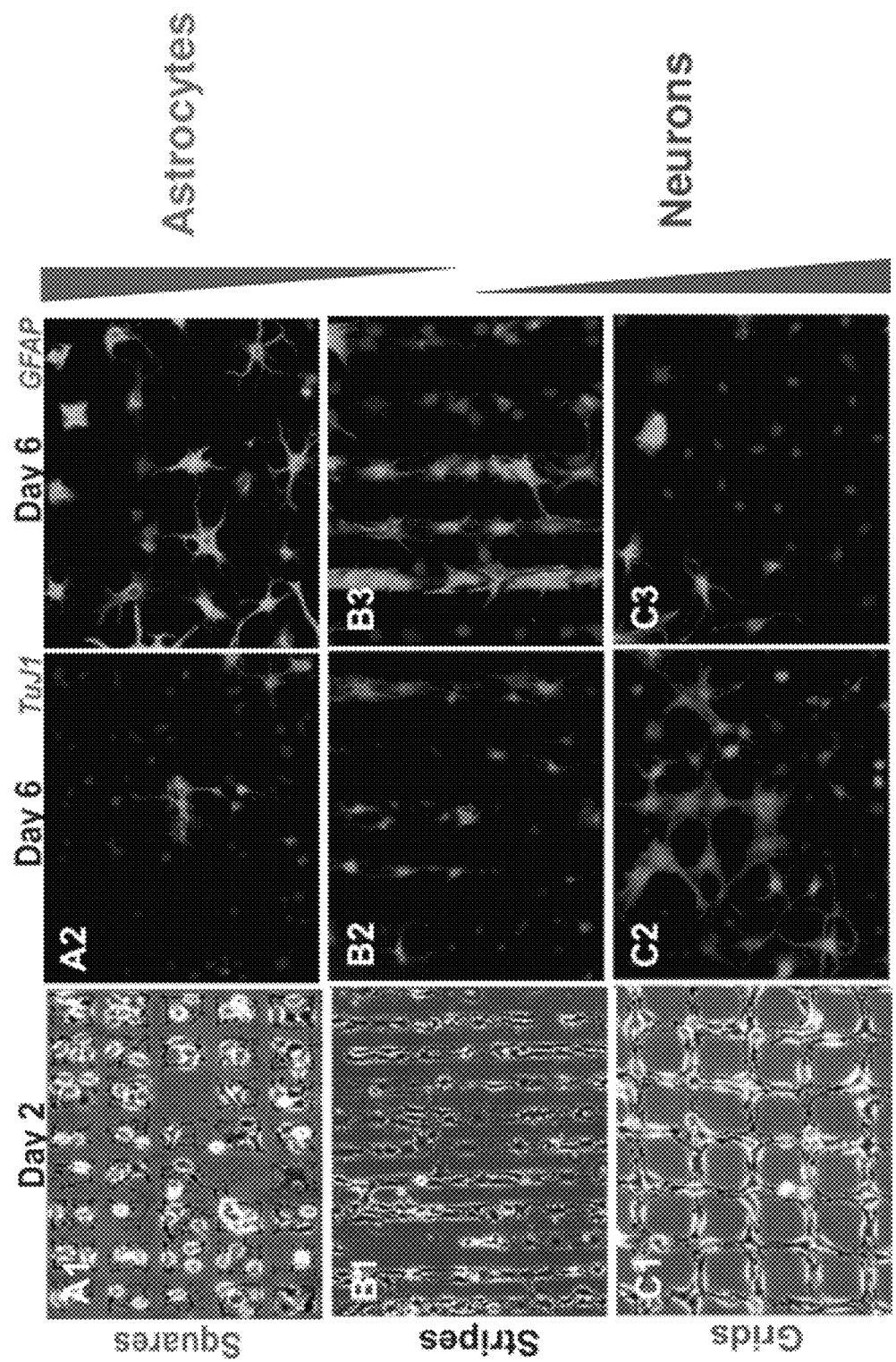
FIG. 2 illustrates growth and differentiation of NSCs on laminin patterns. (A) Phase images of NSCs on squares (A1), stripes (B1), and grids (C1) on Day 2 after seeding. Fluorescent images show extent of neuronal differentiation with the neuronal marker Tuj1 (A2, B2, C2) and glial differentiation with the astrocyte marker GFAP (A3, B3, C3). Scan Bar=50 µm. (B) Quantitative comparison of the percentage of differentiated NSCs expressing the neuronal marker Tuj1 and astrocyte marker GFAP on ECM squares, stripes and grids, six days after seeding.
Figure 2B:
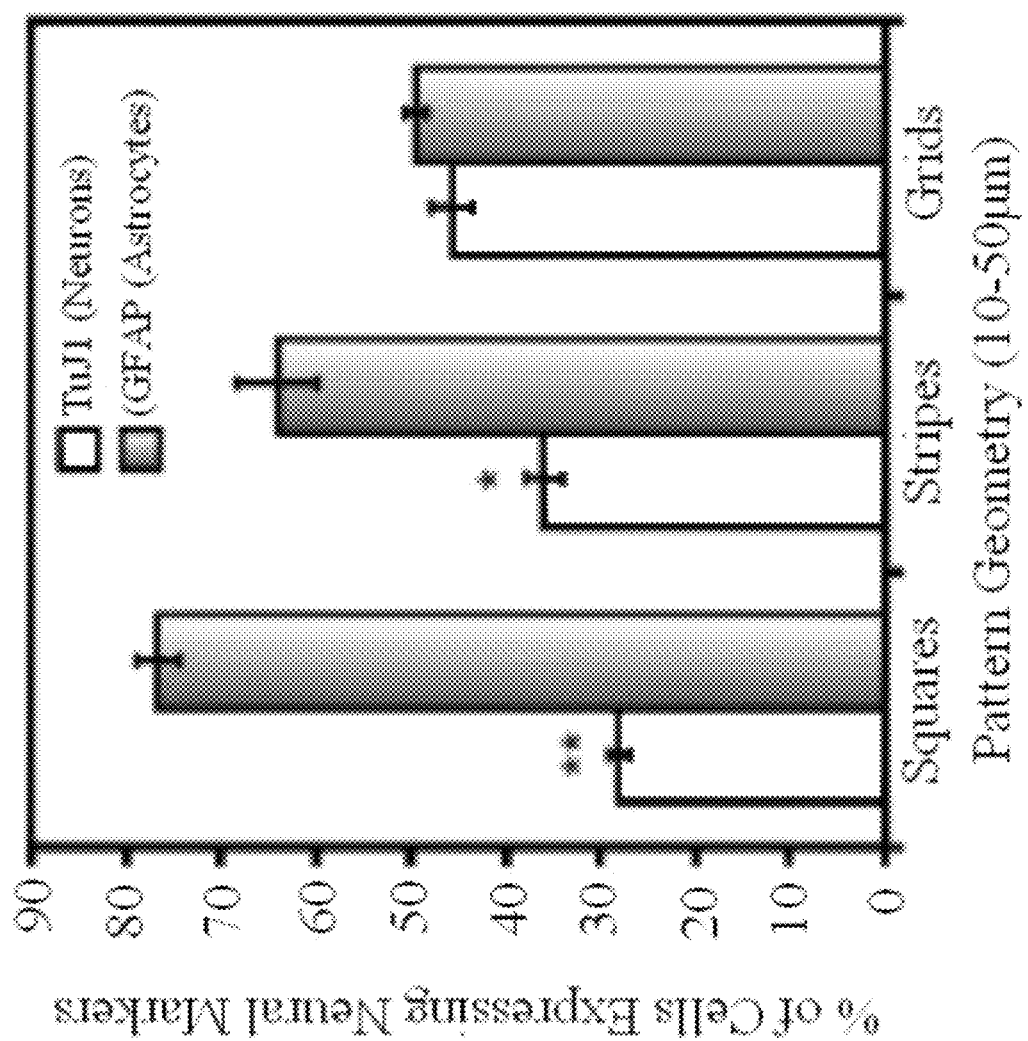

This invention concerns investigation and understanding of the temporal and spatial effects from microenvironmental cues on differentiation of human induced pluripotent stem cell-derived neural progenitor cells (hiPSC-NPCs) into neurons, and in particular their applications in spinal cord injury and neurodegenerative diseases. Induced pluripotent stem cells (iPSCs) are pluripotent stem cells derived from adult somatic cells, for example by inducing expression of specific genes (e.g., Oct-4, Sox2, c-Myc and Klf4) (Amabile, G. and A. Meissner, A., Trends in Molecular Medicine, 2009, 15(2): p. 59-68)[1]. While iPSC-based regenerative medicine offers great opportunities for exploring the devastating deficiencies in neuroscience, mostly because they provide an unlimited source of engraftable neural cells, controlling the stem cell fate towards specific neuronal cell lineage is one of the most pressing concerns to address before their therapeutic application can be fully realized.

The present invention involves generating three-dimensional micron-scale patterns of a novel light-responsive hydrogel to promote the differentiation of hiPSC-derived NPCs into neurons. Many studies have demonstrated the effect of well-defined micropatterned environments on cellular function and behavior. However, current literature has mainly focused on cell studies performed in two-dimensional microenvironments, with limited studies focused on the effect of three-dimensional micropatterns on stem cell behavior. To this end, the present invention, in one embodiment, is directed to neuro-differentiation in a three-dimensional micropatterned culture system, using hydrogels as the choice of biomaterial due to their tissue-like tunable material properties.

The present invention involves synthesizing a novel light-responsive hydrogel with multiple tunable properties. First, the hydrogel contains chemical moieties that can lead to cross-linking of the hydrogel upon exposure to ultraviolet (UV) light. This feature of the hydrogel allows the generation of micropatterns using standard photolithography. Second, the hydrogel contains near infrared (NIR)-cleavage sites, which can be degraded upon exposure to near infrared (NIR) light. This unique attribute of the hydrogel can be utilized to: 1) degrade the hydrogel structure to alter the mechanical properties (e.g., elasticity, porosity), and 2) release a covalently-bound small molecule from the hydrogel backbone to alter intrinsic cellular signaling pathways.

Finally, the geometry/dimension-variant three-dimensional micropatterns of the novel light-responsive hydrogel can be utilized to differentiate hiPSCs-derived NPCs into neurons. The hiPSCs can thus be used to generate and isolate NPCs using protocols known in the art. In addition, the present invention involves generating a greater number of neurons. This platform can be used to produce sub-type specific neurons by using chemical factors that promote specific subtype neuron formation (e.g., dopaminergic and motor neurons). Collectively, the present invention establishes a novel hydrogel-based platform for promoting stem cell neuro-differentiation. This in vitro system can be adapted for in vivo neural transplantation.

In one aspect, the present invention provides a light-responsive hydrogel composition for differentiation of stem cells, comprising:

(a) a polyethylene glycol (PEG) hydrogel;

(b) a UV or NIR triggered chemical adaptor system covalently attaching small molecules to the PEG hydrogel; and (c) small molecules covalently attached to said chemical adaptor system that promote differentiation of neural stem cells into neuronal cells;

wherein said small molecules are cleavable from said chemical adaptor system upon exposure of said system to UV or NIR.

In one embodiment of this aspect, the light-responsive hydrogel composition further comprises an adhesion peptide covalently bonded to the PEG hydrogel.

In another embodiment of this aspect, the adhesion peptide is Ile-Lys-Val-Ala-Val (IKVAV) (SEQ ID NO: 1) or Arg-Gly-Asp (RGD).

In another embodiment of this aspect, the small molecules comprise a signaling pathway inhibitor.

In another embodiment of this aspect, the small molecule signaling pathway inhibitor is Notch inhibitor.

In another embodiment of this aspect, the PEG hydrogel comprises multi-arm poly(ethylene glycol) (PEG)-thiol macromers cross-linked with PEG diacrylate.

In another embodiment of this aspect, the UV or NIR triggered chemical adaptor system comprises a light-sensitive trigger group.

In another embodiment of this aspect, the light-sensitive trigger group comprises a coumarin or 2-nitrobenzyl moiety, which can be cleaved from the chemical adaptor upon irradiation with UV or NIR.

In another embodiment of this aspect, the multi-arm PEG-thiol macromer is a 4-arm macromer. In one embodiment, the 4-arm macromer has a structure of formula:

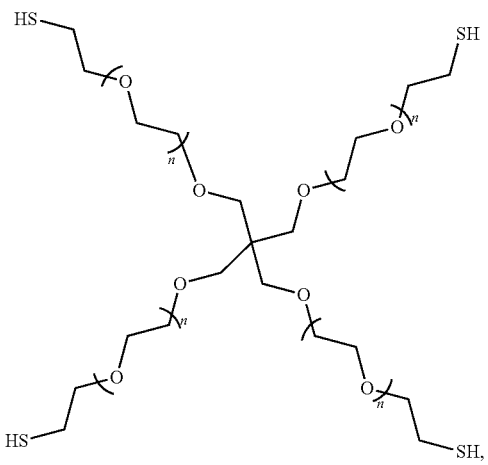

wherein n is an integer dictated by the desired molecular weight of the macromer. In a preferred embodiment, a molecular weight of 10 kDa of this 4-arm PEG-thiol macromer indicates n is 60. In another preferred embodiment, a molecular weight of 2 kDa of this 4-arm PEG-thiol macromer indicates n is 9.

In another embodiment of this aspect, the chemical adaptor has a structure characterized by formula:

wherein the light sensitive molecule includes, but is not limited to, coumarin-based or nitrobenzyl-based molecules that can be cleaved from the chemical adaptor upon irradiation with UV or NIR.

In another embodiment of this invention, the light-sensitive molecule comprises 4,5-dimethoxy-2-nitrobenzyl moiety, which can be cleaved from the chemical adaptor upon irradiation with UV or NIR. Preferably, the light sensitive molecule is 4,5-dimethoxy-2-nitrobenzyl alcohol. In another embodiment, the light-sensitive molecule can consist of a two-photon NIR sensitive coumarin-based moiety (Furuta, T., Wang, S. S.-H., Dantzker, J. L., Dore, T. M., Bybee, W. J., Callaway, E. M., Denk, W., Tsien, R. Y. Proc. Natl. Acad. Sci. USA.,1999, 96: 1193-1200.)

Small molecules suitable for the present invention include any molecules that can promote differentiation of neural stem cells to neuronal cells.

In one embodiment of this aspect, the light-responsive hydrogel system is pre-formed from UV irradiation of the following pre-polymer components: a) a multi-arm poly(ethylene glycol) (PEG)-thiol macromer; b) a PEG diacrylate monomer; c) a PEG acrylate monomer covalently attached with an adhesion peptide chain; and d) a chemical adaptor system covalently connected with a light sensitive group and a small molecule, the chemical adaptor comprises a vinyl group, wherein the pre-polymer components are capable of co-polymerization to form a hydrogel under irradiation with a UV light.

In another aspect, the present invention provides a method for inducing differentiation of pluripotent stem cells into neuronal cells, comprising allowing pluripotent stem cells to infiltrate into a light-responsive hydrogel composition as defined above in a culture medium, and irradiating the hydrogel composition with a UV or NIR light.

In one embodiment of this aspect, the pluripotent stem cells comprise neural stem cells (NSCs).

In another embodiment of this aspect, the pluripotent stem cells comprise human neural stem cells (NSCs).

In another embodiment of this aspect, the pluripotent stem cells are neural progenitor cells (NPCs).

In another embodiment of this aspect, the pluripotent stem cells comprise human induced pluripotent stem cell-derived neural progenitor cells (hiPSC-NPCs).

In another embodiment of this aspect, the hydrogel composition comprises a plurality of pre-polymer components capable of forming three-dimensional micron-scale network under irradiation with a UV light.

In another embodiment of this aspect, the method further comprises in situ polymerization of the pre-polymer components using a UV light into a hydrogel network to encapsulate the stem cells.

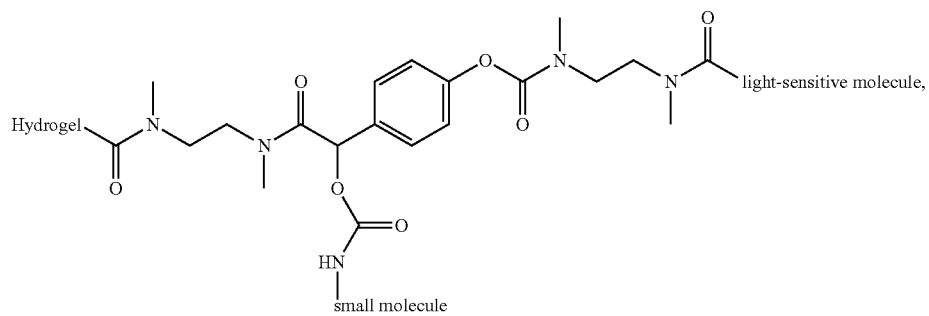

In another embodiment of this aspect, the method further comprises allowing the stem cells to infiltrate into the hydrogel matrix in the presence of a cell-adhesion peptide.

In another embodiment of this aspect, the cell-adhesion peptide is IKVAV (SEQ ID NO: 1) or RGD.

In a preferred embodiment of this aspect, the pluripotent stem cells comprise human induced pluripotent stem cell-derived neural progenitor cells (hiPSC-NPCs).

In another aspect, the present invention provides a method for treating a neurodegenerative disorder or neurological injury, comprising administering to a subject in need of the treatment a therapeutically effective amount of neuron or neuronal cells encapsulated within a light-responsive hydrogel composition as defined above, wherein the neuronal cells encapsulated are capable of differentiating into desired neurons within the hydrogel composition.

In one embodiment of this aspect, the neuronal cells are originated from human induced pluripotent stem cell-derived neural progenitor cells (hiPSC-NPCs).

In another embodiment of this aspect, the neurodegenerative disorder or neurological injury is selected from traumatic brain injury, spinal cord injury, peripheral nerve trauma, Alzheimer's Disease, Parkinson's Disease, Huntington's Disease, epilepsy, stroke and dementias.

In another aspect, the present invention provides a biocompatible implant comprising neurons or neuronal cells differentiated from pluripotent stem cells in a light-responsive hydrogel composition as defined above that has been exposed to light wavelengths effective to release said small molecules.

In a preferred embodiment of this aspect, the pluripotent stem cells comprise human induced pluripotent stem cell-derived neural progenitor cells (hiPSC-NPCs).

The implant may comprise the hydrogel, or the hydrogel contained in an implantable device, including for example a scaffold, matrix or tube.

In another aspect, the present invention provides a kit for preparation of a light-responsive hydrogel composition, comprising the following pre-polymer components: a) a multi-arm poly(ethylene glycol) (PEG)-thiol macromer; b) a PEG diacrylate monomer; c) an acrylate monomer covalently attached to an adhesion peptide chain; and d) a UV or NIR triggered chemical adaptor covalently attached to small molecules, wherein the pre-polymer components are capable of co-polymerization to form a hydrogel composition under irradiation with a UV light.

In one embodiment of this aspect, the UV or NIR triggered chemical adaptor is covalently attached to small molecules capable of promoting differentiation of neural stem cells into neuronal cells upon cleavage from the chemical adaptor when the hydrogel composition is exposed to a UV or NIR light.

In another embodiment of this aspect, the UV or NIR triggered chemical adaptor comprises a light-sensitive trigger group.

In another embodiment of this aspect, the adhesion peptide chain is IKVAV (SEQ ID NO: 1) or RGD.

In other embodiments, the present invention provides methods for promoting the differentiation of NSCs to neurons comprising infiltrating NSCs into a light-responsive hydrogel system suitable to promote the differentiation of NSCs. NSCs are multipotent cells capable of differentiating into neurons and glial cells. In a preferred embodiment, the NSCs are mammalian NSCs. In another preferred embodiment, the NSCs are human NSCs. In a more preferred embodiment, the NSCs are human induced pluripotent stem cell-derived neural progenitor cells (hiPSC-NPCs). NSCs are commercially available or may be obtained from mammalian neural tissue by methods known in the art. This method may be used to generate differentiated cells such as neurons which are useful for methods of regeneration of neural tissue.

In other embodiments, the present invention provides methods of treating or ameliorating a neurodegenerative disorder or a neurological injury comprising administering an effective amount of the biocompatible implant of the present invention to a subject in need of such treatment. Neurodegenerative disorders and neurological injuries include conditions of neuronal cell death or compromise, and include acute and chronic disorders of the central and peripheral nervous system. Such disorders and injuries include, without limitation, traumatic brain injury, spinal cord injury, peripheral nerve trauma, Alzheimer's Disease, Parkinson's Disease, Huntington's Disease, epilepsy, stroke and dementias. The implant can be delivered to a site in the central or peripheral nervous system in proximity to an area of damaged neural tissue by methods known in the art, for example by injection, infusion, or implantation. The implant may be delivered simultaneously with, before, or after another agent including for example, a drug for neural therapy, an anti-inflammatory agent, anti-apoptotic agent, or growth factor.

The present invention provides, in other embodiments, compositions comprising the light-responsive hydrogel system of the invention and a suitable carrier and compositions comprising the implants of the invention and a suitable carrier. The composition can be a pharmaceutical composition that contains a pharmaceutically acceptable carrier. The term "pharmaceutical composition" refers to the combination of an active agent with a carrier, inert or active, making the composition especially suitable for diagnostic or therapeutic use in vivo or ex vivo. The carrier in the pharmaceutical composition must be acceptable in the sense that it is compatible with the active ingredient and capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate.

The present invention also provides kits for use in the differentiation of NSCs and treatment of neurodegenerative disorders and neurological injuries. Such kits include at least a first container containing a composition comprising the light-responsive hydrogel described above in a carrier. The kits may additionally contain solutions or buffers for affecting the delivery of the first composition. The kits may further contain additional containers which contain compositions comprising further agents for treatment of neurodegenerative disorders and neurological injuries including for example, a drug for neural therapy, an anti-inflammatory agent, anti-apoptotic agent, or growth factor. The kits may further contain catheters, syringes or other delivering devices for the delivery of one or more of the compositions used in the methods of the invention. The kits may further contain instructions containing administration protocols for the therapeutic regimens.

EXAMPLES

The present invention is described more fully by way of the following non-limiting examples. Modifications of these examples will be apparent to those skilled in the art.

Methods and Experimental Design

Hydrogels have been used as a tissue engineering platform for stem cell encapsulation since the three-dimensional structure and the high water content closely resemble the native extracellular matrix of the stem cell microenvironment (Tibbitt, M. W. and Anseth, K. S., *Biotech. and Bioeng.*, 2009, 103(4): 655-663.). Synthetic hydrogels based on poly(ethylene glycol) (PEG) are used for cell culture since the bioinertness of PEG prevents non-specific protein adsorption (reducing immune and inflammatory responses) and the versatile chemistry affords the incorporation of chemical and physical cues to control stem cell adhesion (Liu, S. Q., et al., Soft Matter, 2010, 6(1): 67-81; Ulijn, R. V., et al., Materials Today, 2007, 10(4): 40-48.). The present invention involves the synthesis of a novel PEG-based hydrogel system containing both light-responsive moieties and bioactive structures. Additionally, photolithography can be used to create three-dimensional micron-scale patterns of the novel hydrogel. The three-dimensional micropatterns of the novel hydrogels can be used as a culture platform to examine differentiation of human induced pluripotent stem cells-derived neural progenitor cells (hiPSC-derived NPCs). The pattern geometry/dimension of the hydrogel micropatterns and the light-triggered dynamic changes in the mechanical and biochemical composition of the hydrogel play key roles in modulating the NPC neurodifferentiation.

Hydrogels

The hydrogel of the present invention contains four components (outlined in FIG. 3): A) the four-arm poly(ethylene glycol) (PEG)-thiol macromer, B) the PEG diacrylate monomer, C) the IKVAV peptide, and D) the photosensitive 4,5-dimethoxy-2-nitrobenzyl-based chemical adaptor system containing a small molecule inhibitor. This synthetic hydrogel system is based on the covalent crosslinking by the chain polymerization of the multivinyl and thiol-containing pre-polymer components.

Multi-arm PEG-Thiol Macromer and PEG Diacrylate Linker

Figure 3:
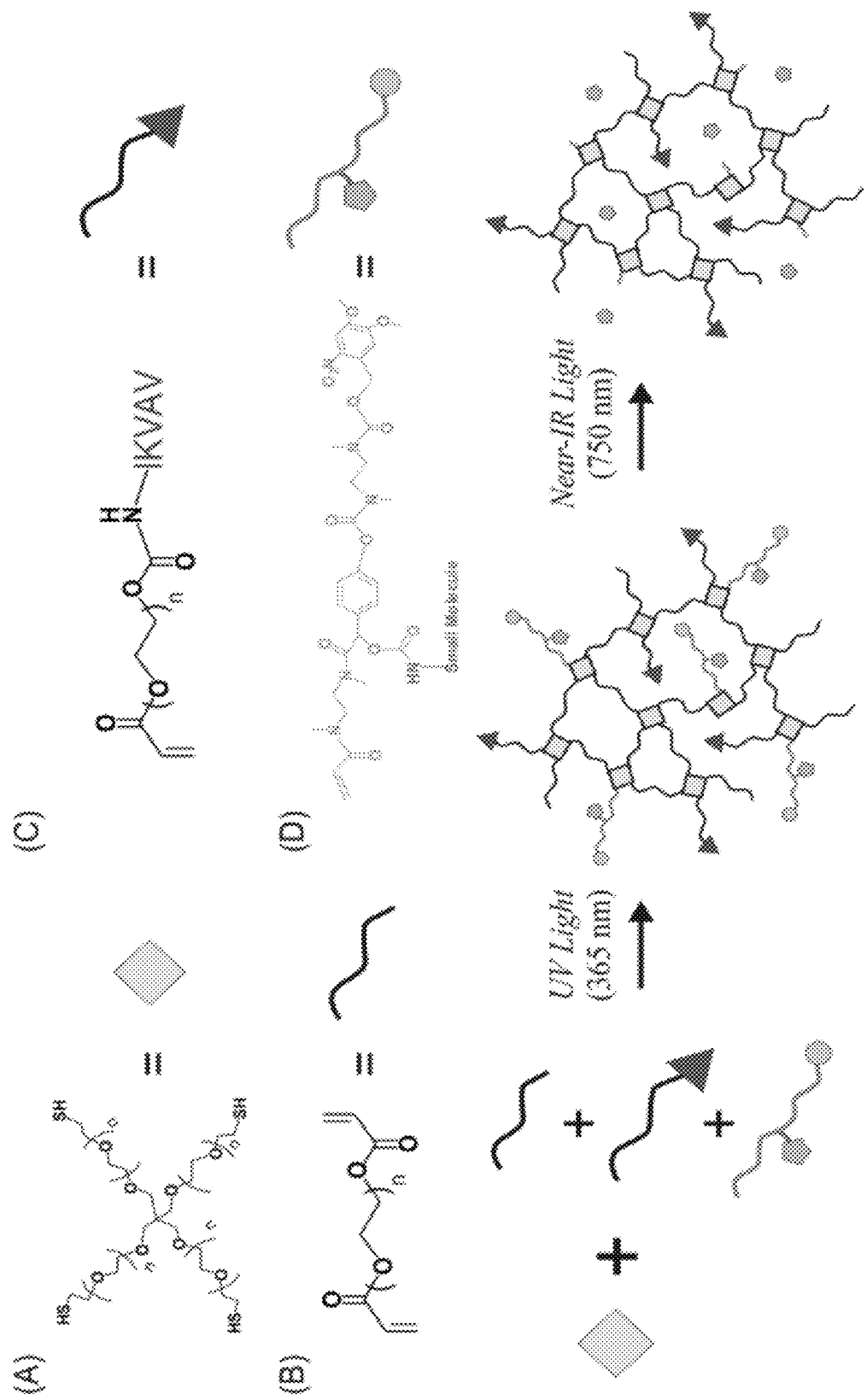
FIG. 3 illustrates novel light-responsive hydrogel design. (A)-(D) The different pre-polymer components of the PEG-based hydrogel. (E) Schematic of UV-mediated cross-linking and NIR-mediated cleavage to release the small molecule Notch inhibitor (blue pentagon).

Multiarm PEG-based hydrogels have been shown to be a means for producing hydrogels (Tan, H., et al., *J. Biomed. Mat. Res. Part A*, 2010, 92A(3): 979-987.). The multi-arm PEG monomers provide both the PEG polymer network to facilitate cell encapsulation and prevent non-specific protein adsorption, while also providing the functional end-groups that can be easily tuned to crosslink the hydrogel and attach biomolecules. In the outlined scheme, the four-arm PEG-thiol monomer is the primary component which forms the underlying backbone of the hydrogel, and the PEG diacrylate is used to link the four-arm PEG monomers to form the gel-like polymer network (FIG. 3). The PEG comonomer solutions, containing complementary reactive groups, are reacted stoichiometrically to form a nearly perfect network by step growth polymerization. The covalent crosslinking for making this hydrogel is based on thiol-ene chemistry utilizing photoirradiation, that is, the pendant thiol end-groups of the four-arm PEG monomer can be covalently linked with pendant alkene groups from another monomer.

IKVAV-containing Monomer

This strategy allows for the immobilization of a wide variety of functional molecules into the hydrogel network, given that the monomer contains an alkene functional end-group. The present invention exploits this thiol-ene chemistry to immobilize the Ile-Lys-Val-Ala-Val (IKVAV) (SEQ ID NO: 1) peptide, which is a known adhesion epitope of the extracellular matrix protein laminin (FIG. 3). The alkene-containing linker portion of the molecule is synthesized, and then is conjugated with the commercially available IKVAV-peptide using.

Photo-responsive Chemical Adaptor System

Figure 4:
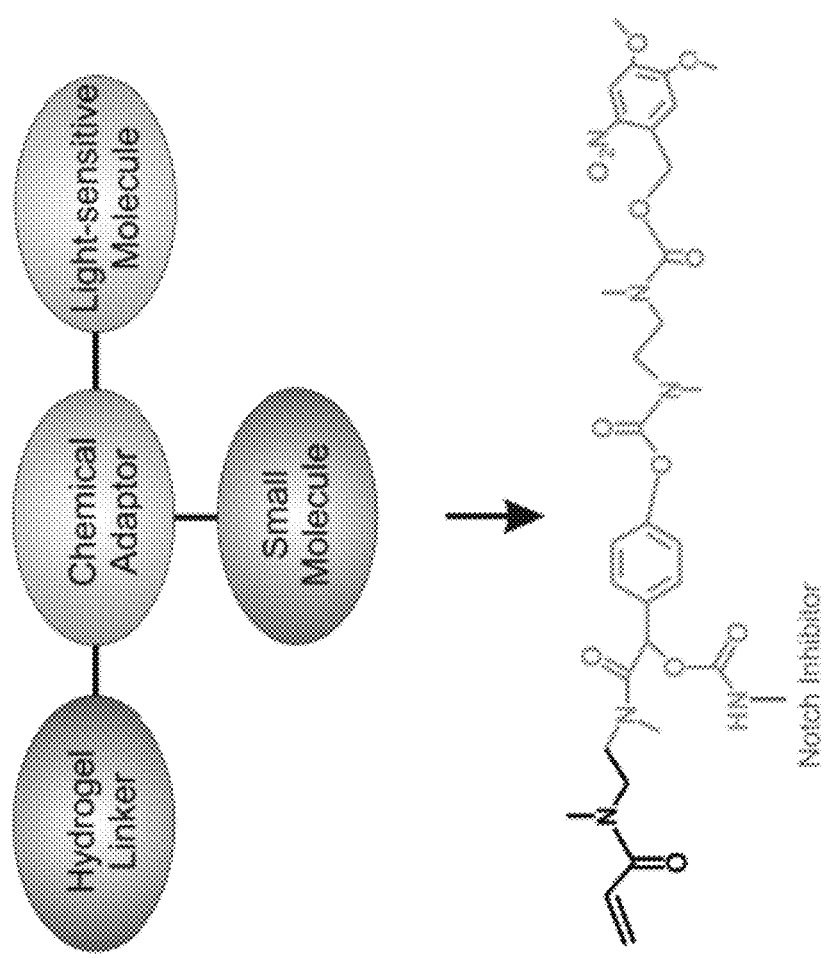
FIG. 4 illustrates scheme and structure of the photo-responsive chemical adaptor system, containing the hydrogel linker (alkene group), light-sensitive molecule (4,5-dimethoxy-2-nitrobenzyl group) and the small molecule (Notch inhibitor).

A light-responsive chemical adaptor system, containing a covalently-attached small molecule, is attached to the four-arm PEG-thiol monomer, as described above (FIG. 3). Gopin et. al. have designed a chemical adaptor system for a tumor-targeting drug delivery application, in which the core of the chemical adaptor was based on a 4-hydroxymandelic acid molecule, which has three functional groups suitable for modification/conjugation (Gopin, A., et al., *Angew. Chem. Int. Ed.*, 2003, 42(3): 327-332.). In the present invention, one of the functional groups of the 4-hydroxymandelic acid molecule is modified to attach it to the hydrogel backbone via the thiol-ene chemistry (FIG. 4). The other two functional groups are modified to attach the light-sensitive molecule (4,5-dimethoxy-2-nitrobenzyl group) and the small molecule (FIG. 4). A purpose of this chemical adaptor is to release a small molecule which can alter the intrinsic cellular signaling pathways of the neural progenitor cells (NPCs) to direct neuronal differentiation. As discussed earlier, inhibition of the Notch pathway has been shown to increase the differentiation into neuronal cells (Ramasamy, S. K. and Lenka, N., *Mol. Cell. Biol.*, 2010, 30(8): 1946-1957.). In turn, this chemical adaptor system is employed to release a Notch inhibitor (gamma-secretase inhibitor, L-685,458; Sigma-Aldrich).

Ultraviolet (UV)-triggered Crosslinking of the Pre-polymer Components

The four pre-polymer components (FIG. 3) are dissolved in aqueous medium (e.g. distilled water, PBS). The relative weight percent of each pre-polymer component is optimized.

Relative to the three linker components (FIG. 3), without being limited to any particular theory, it is presumed that a greater amount of the PEG diacrylate is required, since this monomer is responsible for making two-way cross-links (alkene functional groups on both ends); this can better ensure the mechanical integrity and robustness of the polymer network.

The relative weight percent of the IKVAV-peptide and the chemical adaptor component are adjusted according to desired cellular response (cell spreading vs. small molecule release). After achieving the optimum weight percent, the pre-polymer components are mixed together and the photoinitiator is added to the mixture. Upon irradiation with ultraviolet (UV) light, the photoinitiator decomposes into a free radical and promotes the polymerization reaction. In the above system, DMPA (2,2- dimethoxy-2-phenylacetophenone) is used as the photoinitiator (0.1 wt %) and this cleaves the hydrogen atom from the thiol group of the four-arm PEG (Gupta, N., et al., *Nat. Chem.*, 2010, 2(2): 138-145.). The photo-induced thiol-ene chemistry is a two-step radical chain process that results in addition of the thiol group across the ene double bond of the other monomers (FIG. 3) (Jacobine, A. T., *Radiation Curing in Polymer* Science *and Technology: Photopolymerization Mechanisms*, J. P. Fouassier and Rabek, J. F., eds., 1993, London: Elsevier Applied Science.). The hydrogel of the present invention undergoes a very rapid crosslinking reaction, in which the liquid pre-polymer solution is cured in a short time (approxim. 2 min.) upon exposure to UV light (365 nm, 4.6 mW cm$^2$) (Gupta, N., et al., *Nat. Chem.*, 2010, 2(2): 138-145.). The mild reaction conditions (low exposure time to UV light, tolerance to oxygen and water) are suitable to ensure the stability of the immobilized molecules and peptides within the hydrogel.

Figure 6:
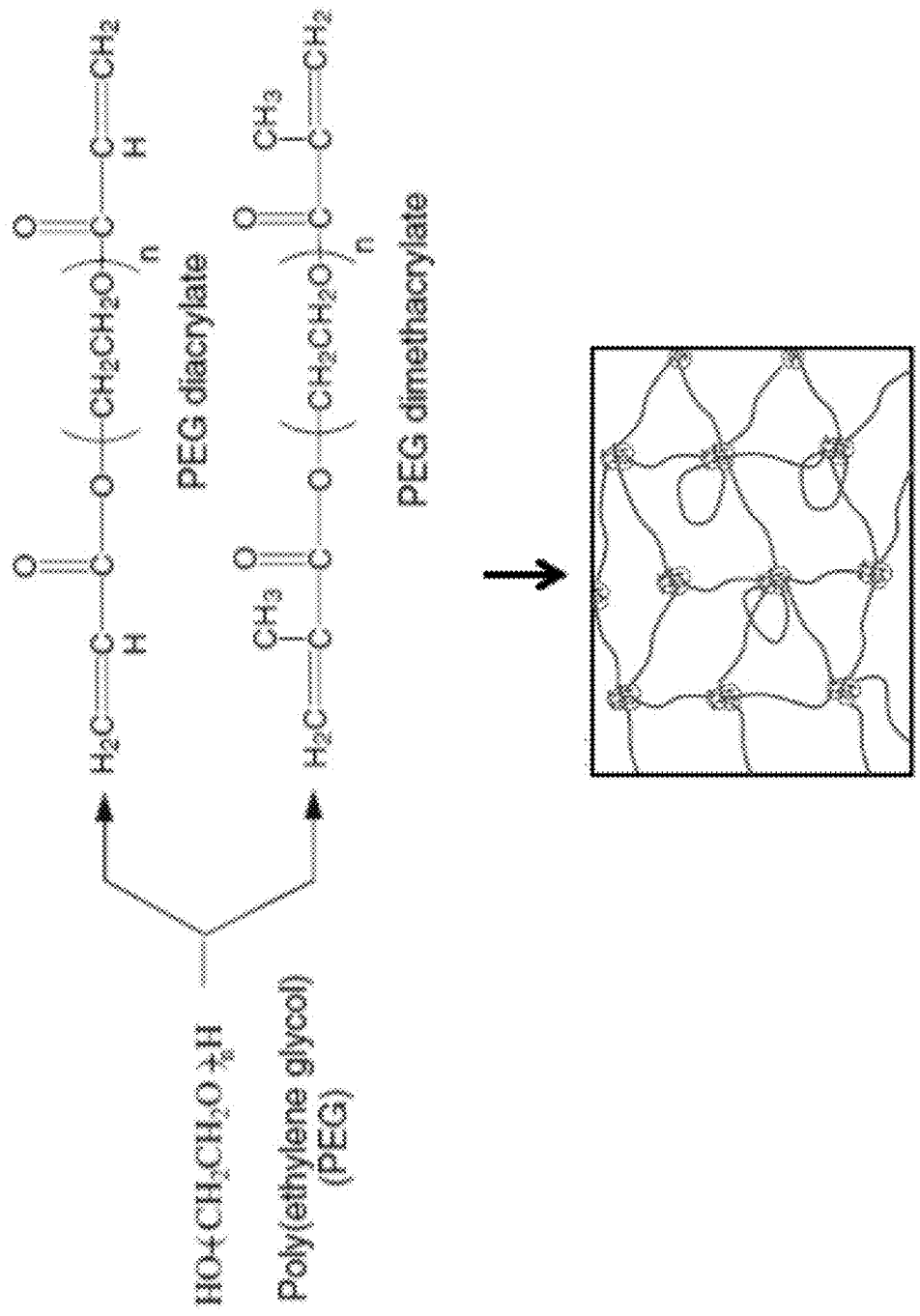
FIG. 6 illustrates formation and 3D structure of PEG hydrogels.
Figure 7:
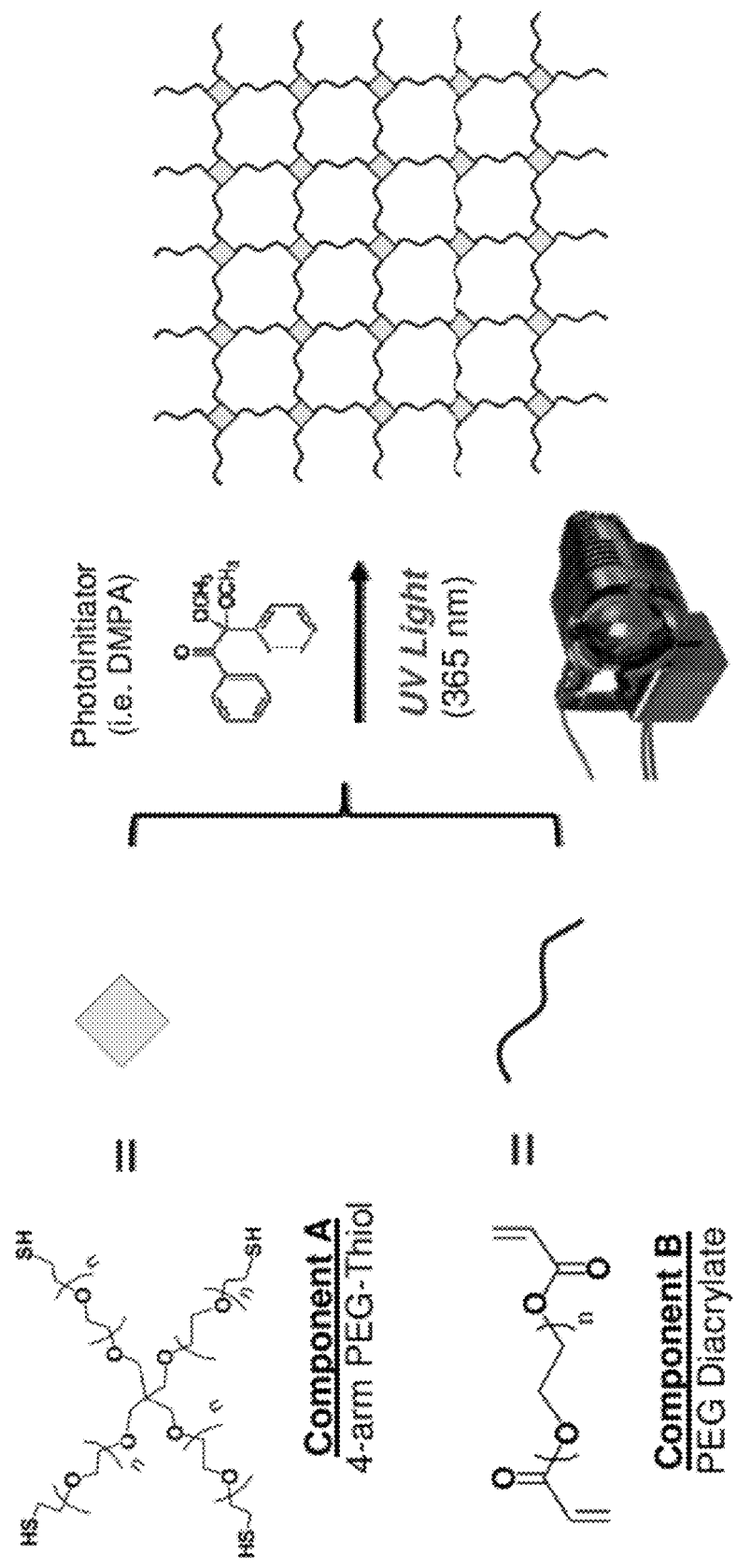
FIG. 7 illustrates synthesis of PEG hydrogels by reaction of a 4-arm PEG thiol macromer with PEG diacrylate.

The hydrogels have 3D structures and high water contents that closely resemble the native cellular microenvironment FIG. 6). Poly(ethylene glycol) (PEG)-based hydrogels are useful for cell culture because i) they can prevent non-specific protein absorption, ii) they have highly tunable mechanical properties, and iii) they have versatile surface chemistry to incorporate chemical/biochemical molecules. As an example, synthesis of the PEG crosslinker from a multi-arm PEG macromer and PEG diacrylate is illustrated in FIG. 7.

Near Infrared (NIR)-triggered Degradation

The novel hydrogel system of the present invention utilizes light of different wavelengths to induce seemingly opposite effects of cross-linking as well as degradation of the hydrogel. As described in the previous section, UV light exposure for about two minutes is sufficient to complete the thiol-ene cross-linking reactions. However, the hydrogel also contains a light-responsive group (4,5-dimethoxy-2-nitrobenzyl) on the chemical adaptor system (FIG. 4). Exposure to light (UV or NIR) cleaves the 4,5-dimethoxy-2-nitrobenzyl group by the light-induced structure change. In contrast to the short time required for cross-linking the hydrogel, the cleavage of this group upon UV light exposure (350 nm) requires longer time and higher power (10 mW/cm$^2$) (Fomina, N., et al., *J. Am. Chem. Soc.*, 2010, 132(28): 9540-9542.). This property of the hydrogel design allows for efficient cross-linking of the hydrogel in a short time without sacrificing the integrity of the light-responsive group. In addition, cleavage of this same light-responsive group has been shown to occur upon irradiation with NIR light (750 nm), over a much longer time scale (in hours) (Fomina, N., et al., *J. Am. Chem. Soc.*, 2010, 132 (28): 9540-9542.).

Figure 5:
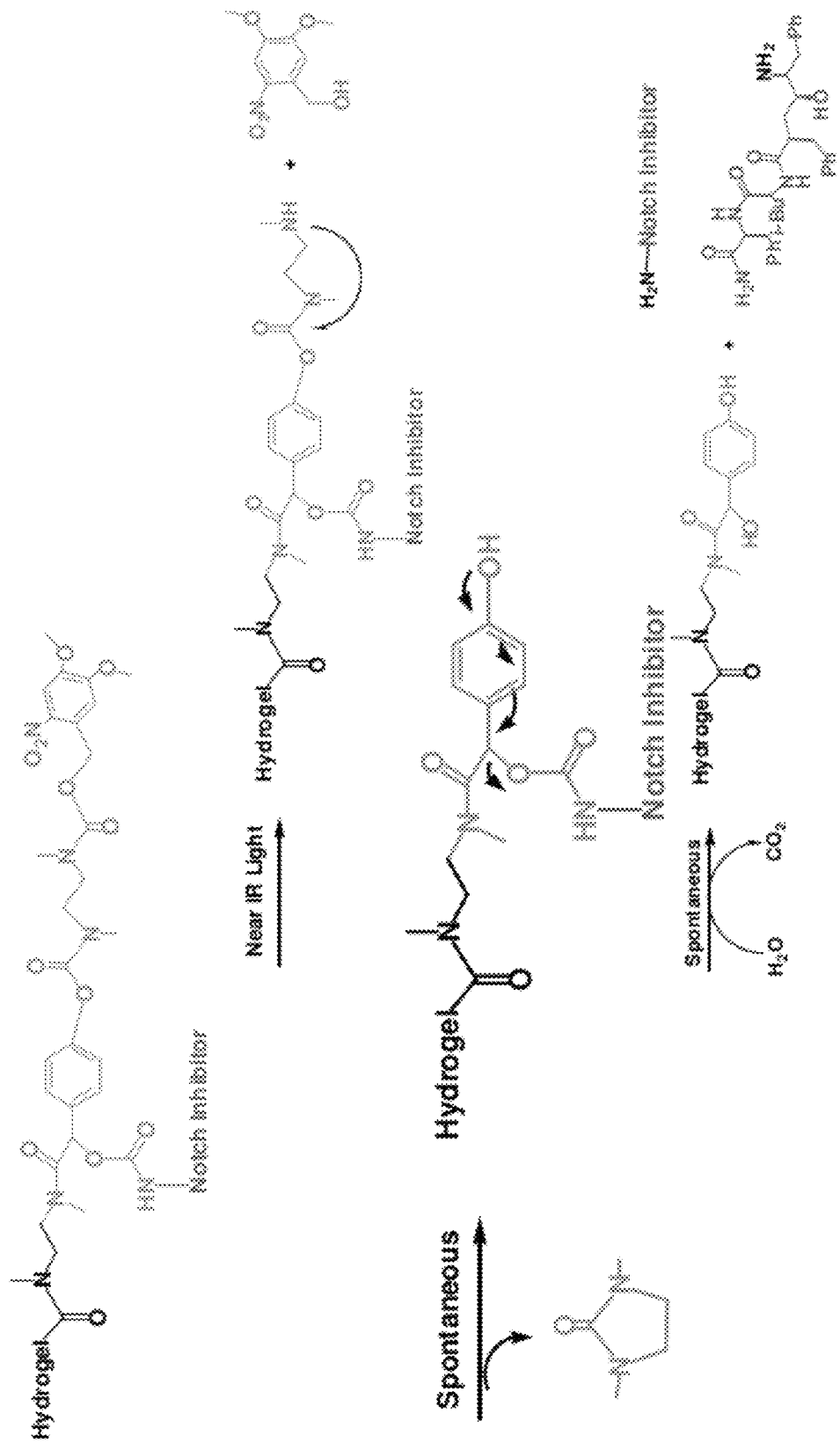
FIG. 5 illustrates mechanism of small molecule (Notch inhibitor) release, initiated by exposure to near infrared (NIR) light.

For biological applications, irradiation with NIR light has several advantages over UV light to cleave the light-responsive group: 1) UV light is damaging to cells since it is absorbed by intrinsic biological chromophores (e.g. DNA), 2) NIR light irradiation relies on a two-photon excitation, which provides higher three-dimensional resolution and tissue penetration, and 3) the transparency of biological media and tissue is enhanced to NIR light (Aujard, I., et al., *Chemistry—A European J.*, 2006, 12(26): 6865-6879.). In turn, the present invention utilizes NIR light to cleave the light-responsive structure and release the attached small molecule (FIG. 5). While the present invention is not limited to any specific theory, presumably cleaving the light-sensitive substrate with NIR light generates a free amine group, which undergoes spontaneously cyclization to form a dimethyl urea derivative and the phenol. The phenol then undergoes spontaneous rearrangement to give a quinone methide intermediate, which is trapped by water to give the benzyl alcohol. This spontaneous rearrangement releases the attached small molecule (Notch inhibitor) into the environment (FIG. 5).

Utilizing Photolithography to Generate Geometry/dimension-variant 3D Micropatterns of the Hydrogel The hydrogel is cross-linked using UV light. This is a valuable means for forming the hydrogel patterns since standard photolithography can be used to cross-link specific regions of the hydrogel (Wosnick, J. H. and Shoichet, M. S., *Chemistry of Materials*, 2007, 20(1): 55-60. Polizzotti, B. D., et al., *Biomacromol.*, 2008, 9(4): 1084-1087.). First, the hydrogel pre-polymer solution (containing a photoinitiator) is spin-coated onto a glass surface to control/optimize the thickness of the hydrogel layer. The ideal thickness of the hydrogel is of such a range that it can encapsulate the cultured cells (approx. 10 μm). Since the pre-polymer solution can be dissolved in a volatile solvent (e.g., chloroform), the solvent evaporates and allow the pre-polymer solution to be efficiently spin-coated.

Next, UV light (365 nm, 4.6 mW/cm$^2$) is passed through a photomask containing the desired micropattern designs (e.g., squares, stripes, and grids, etc.), to generate the lateral features of the micropattern on the hydrogel surface. After curing (for approx. two minutes), the non-cured portion (regions unexposed to UV light) is washed away rigorously with ethanol, which would not affect the integrity of the cured hydrogel due to the change in its chemical properties. The remaining background of the glass substrate (unexposed regions) is passivated with molecules that resist protein/cell adhesion (e.g., PEG-silane). Based on two-dimensional patterning studies, three-dimensional patterns of squares, stripes and grids with lateral dimensions ranging from 10 to 50 μm are made. In order to prepare the hydrogel for cell culture, the hydrogel is washed rigorously by immersion in water with agitation for several hours and then sterilized using an antibiotic solution.

Generation of hiPSC-derived NPCs

The 3D micropatterns of the novel hydrogel system can be used as a culture platform to examine differentiation of hiPSC-derived NPCs. In general, in vitro generation of neurons from pluripotent stem cells requires a stepwise differentiation process: from iPSCs to NPCs to neurons. This culture system can be used to explore the effect of pattern geometry, pattern dimension and the dynamics of the hydrogel on the differentiation process from NPCs to neurons. In turn, established differentiation protocols can first be used to make NPCs from hiPSCs (Axell, M. Z., et al., *J. Neurosci. Meth.*, 2009, 184(2): 275-284.). The NPCs generated from the hiPSCs are then be sorted using flow cytometry and subsequently characterized. These NPC colonies are then expanded and thoroughly characterized using the established NPC markers such as nestin and sox2.

Culturing the hiPSC-derived NPCs within the 3D Hydrogel Micropatterns

One method of stem cell encapsulation involves in situ polymerization, which entails cross-linking the hydrogel around the encapsulated cell. However, free radical polymerization upon photo-polymerization causes drastic changes in the chemical environment around the cell, which is reported to have a negative effect on the viability, proliferation and differentiation of stem cells (Fedorovich, N. E., et al., *Biomat.*, 2009, 30(3): 344-353.). An alternative approach, which is used in the present invention, involves first forming the hydrogel and then allowing the stem cells to infiltrate into the hydrogel matrix. The NPC infiltration is facilitated by the presence of the adhesive IKVAV-epitope in the hydrogel network. In addition, the hydrogel is cultured in previously reported media conditions to facilitate differentiation (DMEM/F12 without bFGF), without added soluble differentiation factors (Axell, M. Z., et al., *J. Neurosci. Meth.*, 2009, 184(2): 275-284.).

Near Infrared (NIR)-triggered Degradation and Release of the Notch Inhibitor

In addition to the effect of geometry and dimension, the effect of the temporal variation in the hydrogel on NPC differentiation is examined by exposing the hydrogel to NIR light. The light-triggered degradation of the hydrogel essentially cleaves the chemical adaptor system. Irradiation with NIR light causes two simultaneous events: 1) release of the Notch inhibitor, and 2) a decrease in the elastic modulus of the hydrogel. In turn, the Notch inhibitor acts as a biochemical cue (down-regulation of the Notch signaling pathway) and degradation of the chemical adaptor system component of the hydrogel acts as a mechanical cue (i.e. softer gel). In addition, the degradation of the hydrogel permits greater cellular movement and increases neurite growth and extension (Hall, P. E., et al., *BMC Neurosci.*, 2008, 9.). Previous studies have reported these factors to be correlated with an increase in neuronal differentiation (Saha, K., et al., *Biophys. J.*, 2008, 95(9): 4426-4438; Borghese, L., et al., STEM CELLS, 2010, 28(5): 955-964.). Since exposure with NIR light requires a longer time to degrade the hydrogel, and ensuring optimal cell viability is crucial, the NIR light is exposed in repeated short time intervals (approx. 15-20 min.) followed by incubation at 37° C. (about 10 min.). Additionally, the elasticity of the hydrogel is characterized using atomic force microscopy (Kloxin, A. M., et al., Biomaterials, 2010, 31(1): 1-8; Domke, J. and Radmacher, M., Langmuir, 1998, 14(12): 3320-3325.). This dynamic control in the present invention allows for a real-time manipulation of the mechanical and biochemical properties of the microenvironment.

Optimizing Mole Ratios for Hydrogel Formation

Using a combinatorial approach to optimize the hydrogel formation for:

| 4-arm PEG Thiol (A) | PEG-Diacrylate Linker (B) |
|---|---|
| 2 kDa | 0.7 kDa |
| 10 kDa | 2 kDa |
| 20 kDa | 4 kDa |
|  | 6 kDa |
|  | 10 kDa |

A systematic approach is necessary to optimize the mole ratio of the different components of the hydrogels to achieve the desired gel consistency and mechanical properties. Table 1 below illustrates how hydrogels with different consistencies can be formed by systematically modulating the weight (and thus the mole ratio) of each gel component, using Component A (4-arm PEG-thiol, 10 kDa) and Component B (PEG-diacrylate, 4 kDa) as an example.

TABLE 1

Optimizing Mole Ratios for Hydrogel Formation

| | Molecular Weight (g/mol) | Weight (g) | Moles |
|---|---|---|---|
| Component A (4-arm PEG) | 10900 | 0.0016 | 1.46424E-07 |
| Component B (PEG diacrylate) | 4110 | 0.00241 | 5.86375E-07 |
| Weight Ratios (B:A) | — | 1.51 | 4.005 |
| % Hydrogel Content (w/v) | | 10.015 | |

| Mol ratio of func groups (alkene:thiol) | alkene | thiol | Mol Ratio of Comps (alkene:thiol) | wt of B (diacrylate alkene) (g) | wt of A (4-arm thiol) (g) | wt ratio (B:A) |
|---|---|---|---|---|---|---|
| 0.5 | 0.25 | 0.25 | 1 | 0.0011 | 0.002918 | 0.377 |
| 0.75 | 0.375 | 0.25 | 1.5 | 0.00145 | 0.002562 | 0.566 |
| 1 | 0.5 | 0.25 | 2 | 0.00172 | 0.002281 | 0.755 |
| 1.25 | 0.625 | 0.25 | 2.5 | 0.00194 | 0.002057 | 0.943 |
| 1.5 | 0.75 | 0.25 | 3 | 0.00212 | 0.001878 | 1.13 |
| 1.75 | 0.875 | 0.25 | 3.5 | 0.00228 | 0.001727 | 1.32 |
| 2 | 1 | 0.25 | 4 | 0.00241 | 0.001596 | 1.51 |

Figure 8:
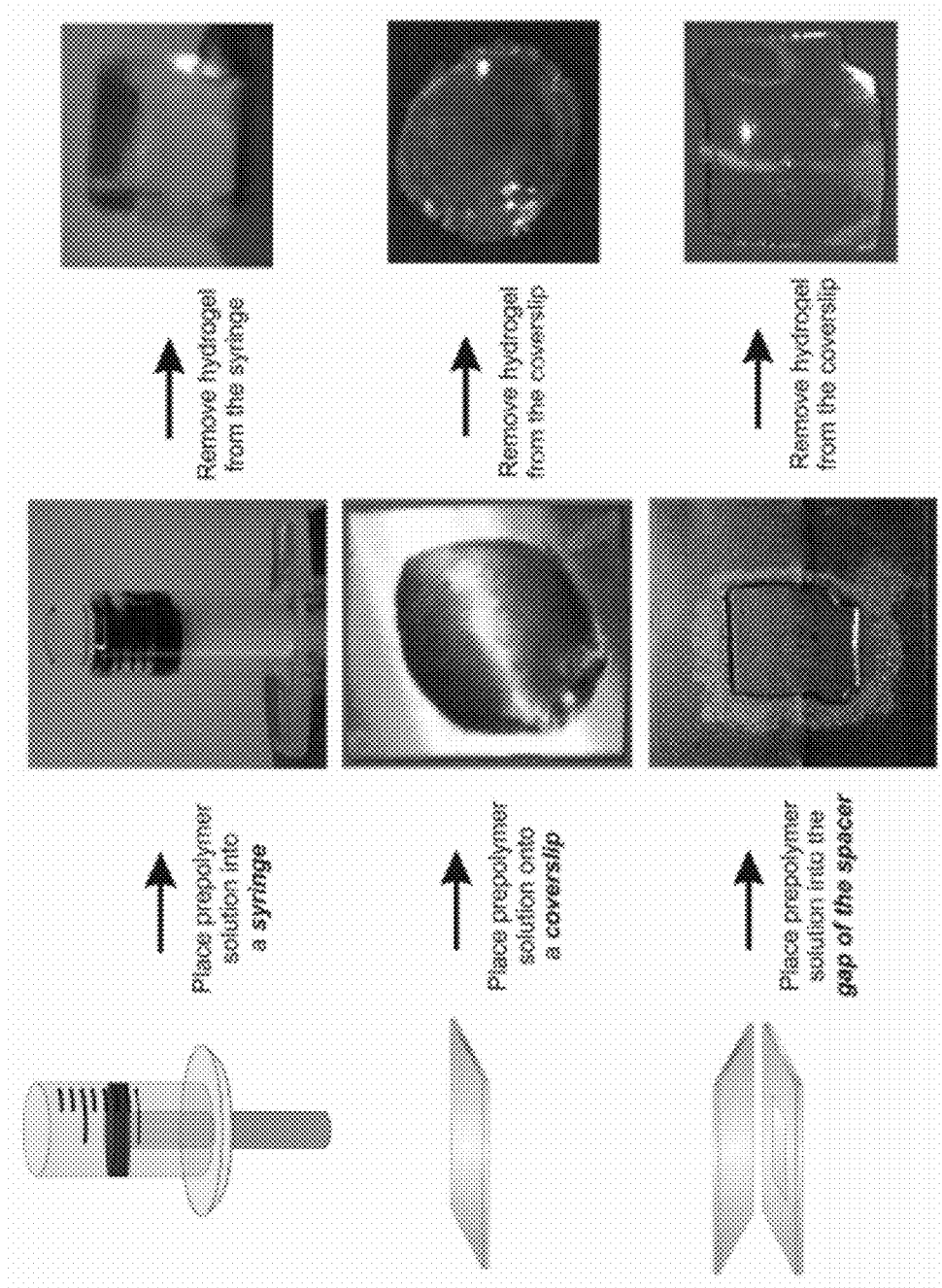
FIG. 8 illustrates hydrogel formation methods.

Illustrative methods for hydrogel formation are illustrated in FIG. 8.

Measuring Mechanical Properties of the Hydrogel

The mechanical properties of the hydrogel were measured using rheometry, which is a methodology to measure the response of a viscoelastic material to applied forces. Based on the data, the elasticity of the hydrogel was determined.

Figure 9:
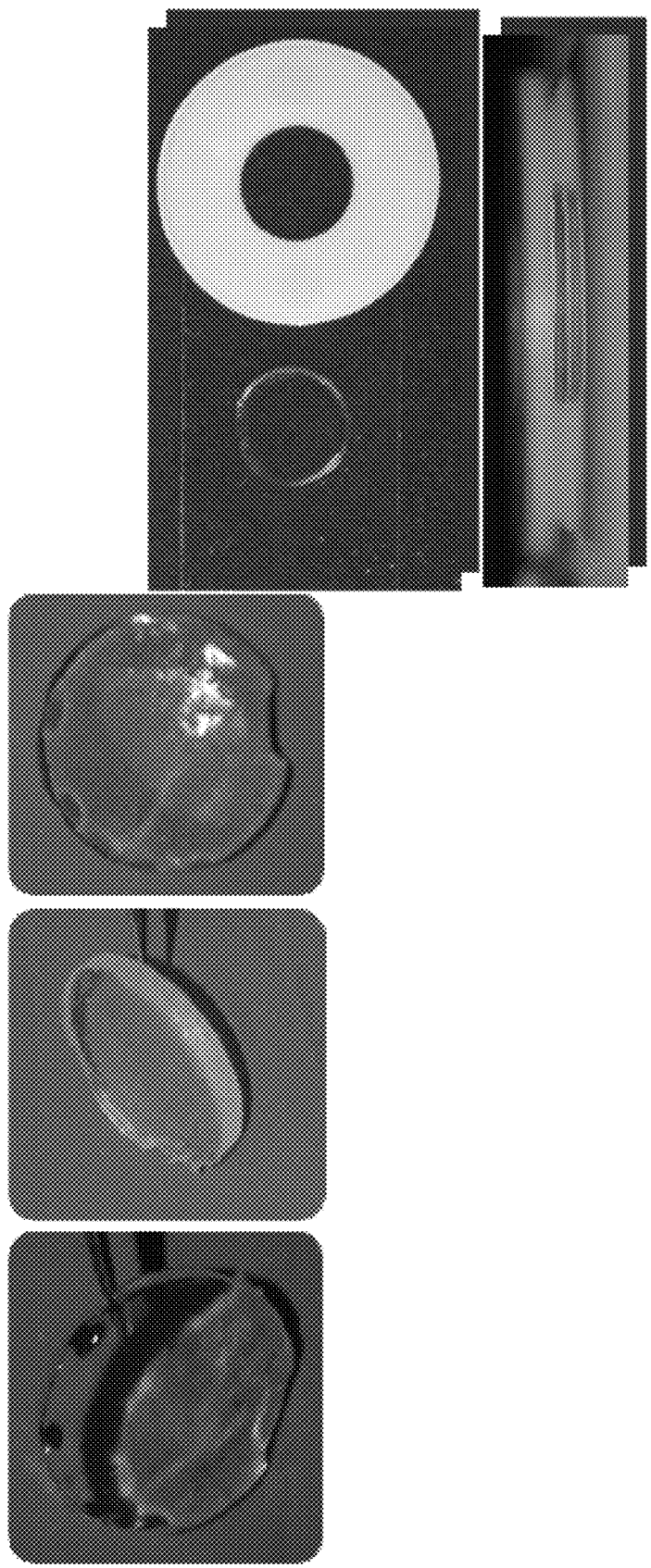
FIG. 9 illustrates hydrogel samples prepared for mechanical measurements.

Illustrative samples prepared for mechanical measurements are shown in FIG. 9.

Hydrogel Elastic Modulus Trends

At a given constant mole ratio of component B (PEG diacrylate, 4 kDa) to component A (4-arm PEG-thiol, 10 kDa), the elastic modulus of the hydrogel increases with increasing amounts of the initial precursor concentration (given as a percent of the weight of solid hydrogel contents [A+B] to volume of the precursor liquid (as shown in Table 2).

At a given constant initial precursor concentration, the elastic modulus of hydrogel also increases with the increasing mole ratio between the amount of component B (PEG diacrylate, 4 kDa) and the amount of component A (4-arm PEG-thiol, 10 kDa), as shown in Table 2.

TABLE 2

Measurement of Hydrogel Elastic Modulus

| | Mole Ratio (B:A) = 3.5 | | |
|---|---|---|---|
| Hydrogel Precursor Concentration (%) | 10 | 12.5 | 15 |
| Elastic Modulus (Pa) | 606 | 1899 | 3489 |
| | 15% Hydrogel Precursor Concentration | | |
| Mole Ratio (B:A) | 2.5 | 3.0 | 3.5 |
| Elastic Modulus (Pa) | 534 | 1056 | 3489 |

A: 4-arm PEG-thiol (10 kDa)
B: PEG diacrylate (4 kDa)

Hydrogel Preparation for Cell Culture

Figure 10:
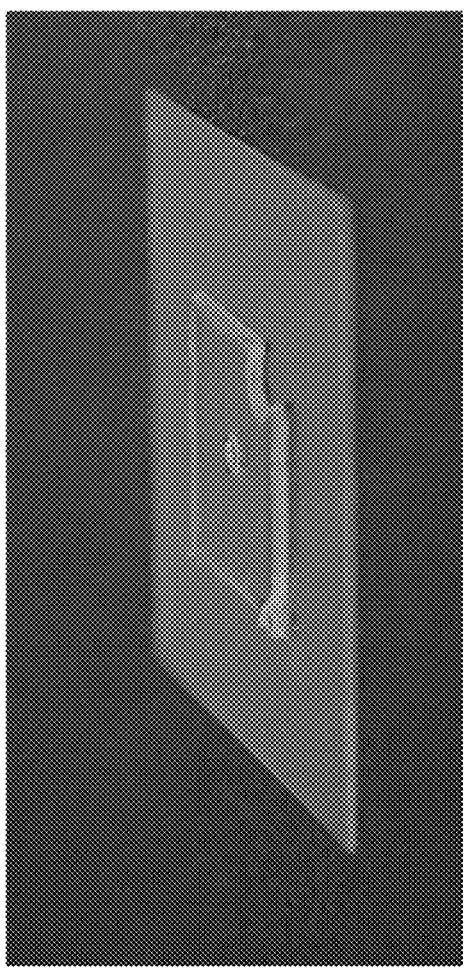
FIG. 10 illustrates hydrogel samples prepared for cell culture.
Figure 10:
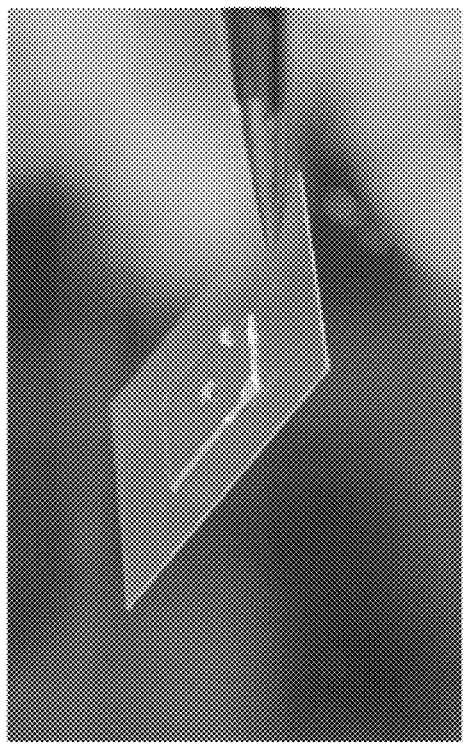

From thin silicon sheets (e.g. 0.01" thickness), any size and shape region can be cut out. This silicon sheet can be used as a spacer, wherein the hydrogel precursor solution can be introduced into the vacant space (illustrated in bottom row of FIG. 8). Illustrative examples for hydrogel preparation for cell culture are shown in FIG. 10.

In summary, the present invention provides a novel light-responsive hydrogel system which has the following characteristics: (1) it undergoes crosslinking under UV-irradiation; (2) it undergoes degradation under near IR (NIR) irradiation; (3) it contains cell adhesion binding peptides (i.e. IKVAV-epitope of laminin); (4) it decreases in elastic modulus upon degradation; (5) it releases small molecule (Notch Inhibitor).

The foregoing examples and description of the preferred embodiments should be interpreted as illustrating, rather than as limiting the present invention as defined by the claims. All variations and combinations of the features above are intended to be within the scope of the following claims. All references cited herein are incorporated herein in their entireties.

What is claimed is:

1. A light-responsive hydrogel composition for differentiation of stem cells, comprising:
   (a) a photo cross-linked polyethylene glycol (PEG) hydrogel;
   (b) a UV or NIR triggered chemical adaptor system covalently attaching small molecules to the PEG hydrogel and comprising a UV or NIR light-sensitive trigger group molecule; and
   (c) small molecules covalently attached to said chemical adaptor system that promote differentiation of neural stem cells into neuronal cells;
   wherein said hydrogel composition has the structure:

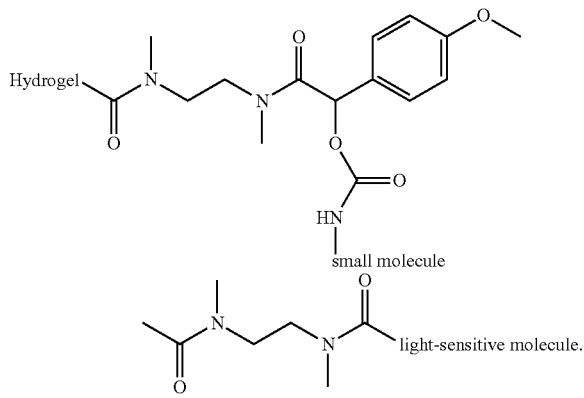

2. The light-responsive hydrogel composition of claim 1, further comprising an adhesion peptide covalently bonded to the PEG hydrogel.

3. The light-responsive hydrogel composition of claim 2, wherein the adhesion peptide is Ile-Lys-Val-Ala-Val (IKVAV) (SEQ ID NO: 1) or Arg-Gly-Asp (RGD).

4. The light-responsive hydrogel composition of claim 1, wherein said small molecules comprise a signaling pathway inhibitor.

5. The light-responsive hydrogel composition of claim 4, wherein the small molecule signaling a pathway inhibitor is Notch inhibitor.

6. The light-responsive hydrogel composition of claim 1, wherein the PEG hydrogel comprises multi-arm poly(ethylene glycol) (PEG)-thiol macromers cross-linked with PEG diacrylate.

7. The light-responsive hydrogel composition of claim 1, wherein the light-sensitive trigger group comprises a coumarin or 2-nitrobenzyl moiety, which can be cleaved from the chemical adaptor system upon irradiation with UV or NIR.

8. A method for inducing differentiation of pluripotent stem cells into neuronal cells, comprising allowing pluripotent stem cells to infiltrate into a light-responsive hydrogel composition of claim 1 in a culture medium, and irradiating the hydrogel composition with a light wavelength that triggers cleavage of said small molecule from said chemical adaptor.

9. The method of claim 8, wherein the pluripotent stem cells comprise neural stem cells (NSCs).

10. The method of claim 8, wherein the pluripotent stem cells comprise human induced pluripotent stem cell-derived neural progenitor cells (hiPSC-NPCs).

11. A biocompatible implant comprising neurons or neuronal cells differentiated from pluripotent stem cells in a light-responsive hydrogel composition of claim 1 that has been exposed to light wavelengths effective to release said small molecules.

12. The biocompatible implant of claim 11, wherein the pluripotent stem cells comprise human induced pluripotent stem cell-derived neural progenitor cells (hiPSC-NPCs).

13. A kit for preparation of a light-responsive hydrogel composition, comprising the following pre-polymer components: a) a first component comprising a multi-arm poly(ethylene glycol) (PEG)-thiol macromer; b) a second component comprising a PEG diacrylate monomer; c) a third component comprising an acrylate monomer covalently attached to an adhesion peptide chain; and d) a fourth component comprising a UV or NIR triggered chemical adaptor covalently attached to small molecules and comprising a UV or NIR light-sensitive trigger group molecule wherein the fourth component has the structure:

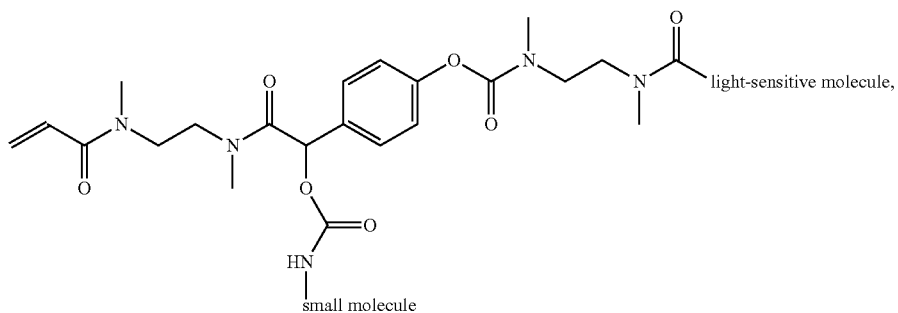

wherein the pre-polymer components are capable of co-polymerization to form a hydrogel composition under irradiation with a UV light wavelength different than the wavelengths that trigger said chemical adaptor.

14. The kit of claim 13, wherein the chemical adaptor is covalently attached to small molecules capable of promoting differentiation of neural stem cells into neuronal cells upon cleavage from the chemical adaptor when the hydrogel composition is exposed to a light wavelength that triggers cleavage of said small molecule from said chemical adaptor.

15. The PEG hydrogel kit of claim 13, wherein the adhesion peptide chain is IKVAV (SEQ ID NO: 1) or RGD.

* * * * *

SEQUENCE LISTING

<160> NUMBER OF SEQ ID NOS: 1

<210> SEQ ID NO 1
<211> LENGTH: 5
<212> TYPE: PRT
<213> ORGANISM: Artificial
<220> FEATURE:
<223> OTHER INFORMATION: Synthetic peptide

<400> SEQUENCE: 1

Ile Lys Val Ala Val
1               5